(12) United States Patent
Hermansson et al.

(10) Patent No.: US 6,669,678 B2
(45) Date of Patent: Dec. 30, 2003

(54) ABSORBENT ARTICLE PROVIDED WITH A BELT

(75) Inventors: Kent Hermansson, Västra Frölunda (SE); Kenneth Strannemalm, Floda (SE); Katharina Karlsson, Härryda (SE)

(73) Assignee: SCA Hygiene Products AB, Gothenburg (SE)

( * ) Notice: Subject to any disclaimer, the term of this patent is extended or adjusted under 35 U.S.C. 154(b) by 257 days.

(21) Appl. No.: 09/814,941

(22) Filed: Mar. 23, 2001

(65) Prior Publication Data

US 2001/0034511 A1 Oct. 25, 2001

Related U.S. Application Data

(60) Provisional application No. 60/201,309, filed on May 2, 2000.

(51) Int. Cl.[7] ............................................... A61F 13/15
(52) U.S. Cl. ........................................................ 604/392
(58) Field of Search .............................. 604/386–392, 604/398

(56) References Cited

U.S. PATENT DOCUMENTS

| | | | | |
|---|---|---|---|---|
| 5,549,593 A | * | 8/1996 | Ygge et al. | 604/391 |
| 5,685,873 A | * | 11/1997 | Bruemmer | 604/385.24 |
| 6,306,121 B1 | * | 10/2001 | Damaghi et al. | 604/385.3 |
| 6,432,099 B2 | * | 8/2002 | Ronnberg | 604/392 |

FOREIGN PATENT DOCUMENTS

| | | |
|---|---|---|
| EP | 287388 | 10/1988 |
| EP | 409307 | 1/1991 |
| EP | 528282 | 2/1993 |
| EP | 605012 | 7/1994 |
| FR | 2586558 | 3/1987 |
| WO | 95/19753 | 7/1995 |

\* cited by examiner

*Primary Examiner*—Weilun Lo
*Assistant Examiner*—Michele Kidwell
(74) *Attorney, Agent, or Firm*—Burns, Doane, Swecker & Mathis, L.L.P.

(57) ABSTRACT

Absorbent article, such as a diaper and an incontinence guard, comprising a liquid-pervious topsheet (2), a liquid-impervious backsheet (3), and an absorbent body (4). The article exhibits a front portion (5), a rear portion (6), a crotch portion (7), and a belt (9, 9') attached to or intended to be attached to the rear portion (6) and to the front portion (5), so that the article assumes a pant-like shape. On both the outside and the inside, at least one belt portion (9') carries a receiving material (12, 13) which can serve as a receiving area for an attachment material (10) on a second belt portion (9) and on one or several attachment means (8, 8') attached to the front portion (5) of the article. The receiving area (12, 13) also enables reattachment of said attachment material. The attachment material (8a, 8b, 8'a, 8'b) is arranged on both a first and second main surface of at least one of the attachment means when this is in an unfolded position, wherein the belt (9, 9') carries the receiving material (12, 13) across substantially its entire outside and inside.

12 Claims, 4 Drawing Sheets

ABSORBENT ARTICLE PROVIDED WITH A BELT

This application claims priority under 35 U.S.C. §§119 and/or 365 to 0001176-7 filed in Sweden on Mar. 31, 2000 and to U.S. Provisional Application No. 60/201,309. filed on May 2, 2000, the entire contents of which are hereby incorporated by reference.

TECHNICAL FIELD

The present invention relates to an absorbent article, such as a diaper and an incontinence guard, comprising a liquid-pervious topsheet, a liquid-impervious backsheet and an absorbent body enclosed therebetween, wherein the article exhibits a front portion, a rear portion, and a crotch portion located therebetween, and flier exhibits a belt, attached to or intended to be attached to the rear portion and to the front portion of the article, in such a way that the article assumes a pant-like shape where the belt constitutes a part of the waist portion of the pant.

BACKGROUND OF THE INVENTION

Diapers and incontinence guards for incontinent adults usually have a garment portion holding an absorbent body in place against the user's body, and attachment means which hold the garment portion in place also when the user is moving. A common type of attachment means is adhesive tape tabs or hook and loop fasteners, which directly attach the front and rear portions of the absorbent article to each other.

It is also previously known, e.g. through EP-A-0 287 388, BP-A-0 409 307, EP-A-0 528 2282, EP-A-0 605 012 and FR-A-2 586 558, to attach the front and rear portions of the article to each other by means of a belt, wherein the possibilities to adjust the fit are improved. Depending on the type of attachment means, different types of receiving surfaces, which are to cooperate with the attachment means, are utilised. Another advantage with belt diapers is that a user which is standing up, when putting the diaper on, first can fix the belt around his/her waist and then raise the absorbent portion of the diaper which is hanging down between his/her legs and fix its attachments means to the belt. In many cases, users having a reduced coordination or ability to move perceive such a dressing as being easier than it would be to put on a conventional "all-in-one" diaper or pant diaper.

Furthermore, WO 95/19753 discloses an absorbent article, such as a disposable diaper, an incontinence guard, a pant diaper or the like. The absorbent article comprises a containment arrangement comprising a liquid-pervious frontsheet, a liquid-impervious backsheet, an absorbent core arranged between the front- and backsheet, a first attachment arrangement and a second attachment arrangement. The attachment system disclosed in WO 95/19753 comprises that both the belt and the opposite waist portion of the diaper have attachment means on both the inside and the outside, and is in this way reported to enable the carrier to choose between putting on the article as a conventional diaper, as a pant diaper, or as a belt diaper. Furthermore, the attachment system is claimed to be designed for ensuring an easy removal and change of the diaper, and an easy inspection of whether the diaper has been soiled.

However, the previously known belt diapers can be perceived as being associated with certain problems.

Unlike infants, incontinent adults may have body sizes and shapes within a very wide range. The previously known diapers often have first attachment means of a limited area on one of the belt portions and second attachment means of a limited area on the other belt portion. Consequently, in order to obtain an attachment of the first attachment means to the second attachment means, it is required that the relatively small attachment areas of the first and second attachment means come into contact with each other. Besides resulting in demands on precision when fixating the belt, difficulties in adapting the belt length to different body sizes will arise. The previously known absorbent belt products often exhibit similar problems when locally delimited attachment means on the front portion of the diaper are to be attached to corresponding locally delimited attachment means on the belt in order to complete the dressing.

When nursing homes and the like are concerned, it sometimes occurs that incontinent adult users of belt diapers participate in toilet training or in the daytime more or less independently take care of their toilet visits. With the previously known belt diapers, there is a large risk that the portion of the diaper hanging down after having been released from the belt accidentally is dipped down into the toilet bowl when the user sits down or gets up. This is of course not desirable.

OBJECT AND MOST IMPORTANT FEATURES OF THE INVENTION

Accordingly, an object of the present invention is to achieve an absorbent article which eliminates the problem with the article accidentally being dipped down into a toilet bowl in connection with toilet training or a user's independent toilet visits, which article furthermore can be adapted to most occurring body sizes and shapes, and which article in addition optionally can be put on and taken off as a belt product, an "all-in-one" product, on in a similar fashion as a pant diaper.

The object is achieved by means of an absorbent article, such as a diaper or an incontinence guard, which comprises a liquid-pervious topsheet, a liquid-impervious backsheet, and an absorbent body enclosed therebetween. The article exhibits a front portion, a rear portion, and a crotch portion located therebetween, and further a belt, attached to or intended to be attached to the rear portion and to the front portion of the, article in such a way that the article assumes a pant-like shape where the belt constitutes a part of the waist portion of the pants. Thereby, at least a first belt portion carries a receiving material both on the face which is to constitute the outside and on the face which is to constitute the inside of the belt, which receiving material can serve as a receiving area for an attachment material arranged on a second belt portion and as a receiving area for an attachment material arranged on one or several attachment means attached to the front portion of the article which comprise a first main surface and an opposite, second main surface, and wherein the receiving surface also enables reattachment of the attachment material. According to the invention, the attachment material on the attachment means is arranged on both the first and the second main surface of at least one of the attachment means when it is in an unfolded position, wherein the, belt portion or belt portions carry/carries the receiving material across substantially its/ their entire outside and inside.

BRIEF DESCRIPTION OF THE DRAWINGS

In the following, the invention will be described in greater detail with reference to the attached drawings, in which FIG. 1 schematically shows a perspective view of an absorbent article according to a preferred embodiment of the invention, with a cut-out portion and seen from the face of the article which is intended to stand in contact with the skin of a user, FIG. 2 schematically, in a cross-sectional view through the line II—II in FIG. 1, shows the attachment means of the absorbent article, wherein one of the attachment means is in an unfolded position, whereas the other attachment means is in a folded-in position, and the thicknesses of the different material layers for reasons of clarity have been exaggerated, FIG. 3 schematically shows the absorbent article in FIG. 1 with its belt applied around the belt of a user, FIG. 4 schematically shows the absorbent article in FIG. 3 in a suspended position, which eliminates the problem of the article being accidentally dipped into a toilet bowl in connection with toilet training or a user's independent toilet visits, FIG. 5 schematically shows the absorbent article in FIG. 3 after having been completely dressed on the user as a belt product, and FIG. 6 schematically shows the absorbent article in FIG. 1 after having been completely dressed on the user as an "all-in-one" product, alternatively in a similar fashion as a pant diaper.

DESCRIPTION OF EMBODIMENTS

Figure 1:
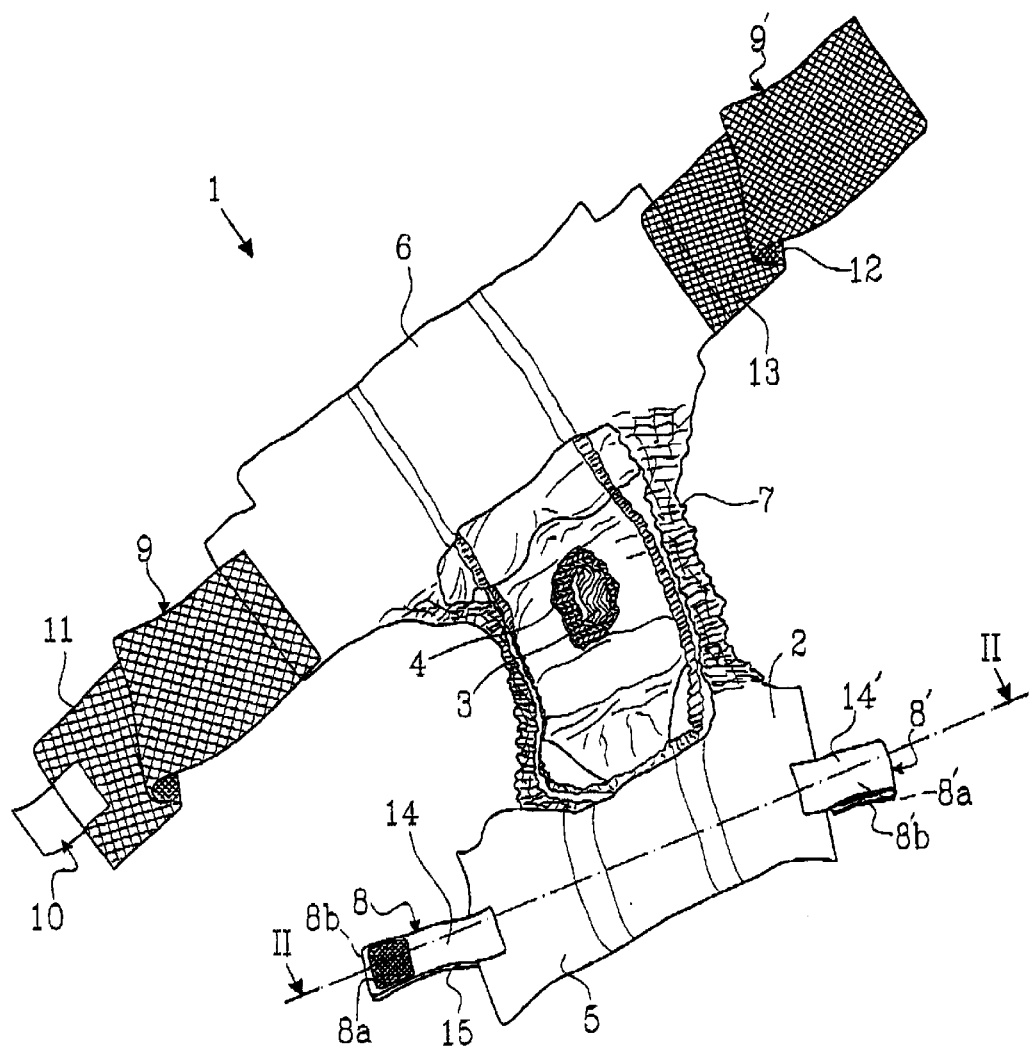

FIG. 1 shows a preferred embodiment of an absorbent article according to the invention in form of an incontinence diaper 1 comprising a liquid pervious topsheet 2, a liquid-impervious backsheet 3, and an absorbent body 4 enclosed therebetween. The liquid-pervious topsheet 2 can consist of a nonwoven material, e.g. a spunbond material of continuous filaments, a meltblown material, or a bonded, carded fibre material. The liquid-impervious backsheet 3 can consist of a plastic film, a nonwoven material coated with a liquid-arresting material, or a hydrophobic nonwoven material which resists liquid penetration.

The topsheet 2 and the backsheet 3 have a slightly larger extension in the plane than the absorbent body 4 and extend outside its edges. The topsheet 2 and the backsheet 3 are mutually interconnected within the extending portions, for example by means of glueing or welding with heat or ultrasonic.

The absorbent body 4 can be of any conventional type. Examples of commonly occurring absorption materials are cellulose fluff pulp, tissue layers, highly absorptive polymers (so-called superabsorbents), absorbent foam materials, absorbent nonwoven materials, and the like. It is common to combine cellulose fluff pulp with superabsorbents in an absorbent body. It is also common with absorbent bodies constituted of layers of different materials having different properties when liquid acquisition ability, distribution ability and storage ability are concerned. This is well known to the skilled person and does not have to be described in detail. The thin absorbent cores which are common in for example baby diapers and incontinence guards often consist of a compressed mixed or layered structure of cellulose fluff pulp and superabsorbent.

The diaper is intended to enclose the lower portion of the torso of the user as a pair of absorbent pants. It exhibits a front portion 5 intended to be facing forwards on the user during use, a rear portion 6 intended to be facing backwards on the user during use, and a narrower crotch portion 7 located between the front and rear portion, which is intended to be applied in the crotch of the user between his/her legs.

A pair of belt portions 9, 9' are with one of their ends attached to, e.g. glued or ultrasonically welded to, the rear portion 6 of the diaper. The width of the belt potions 9, 9' is advantageously between 5–20 cm, preferably between 7–15 cm. On the face which is to constitute the outside and on the face which is to constitute inside of the belt, at least one of the belt portions 9' carries a receiving material 12, 13 which can serve as a receiving area for an attachment material 10 arranged on the other belt portion 9. Accordingly, the belt portions 9, 9' are intended to be attached to each other by means of the attachment material 10, for example a hook material, which is received on the opposite belt portion. Instead of hook material, optionally another attachment material can be used, such as adhesive tape.

The receiving material 12, 13 of the belt should also serve as a receiving area for an attachment material arranged on one or several attachment elements 8, 8' attached to the front portion 5 of the article. These attachment elements 8, 8' comprise a first main surface, and an opposite, second main surface and are intended to be attached to the belt portions 9, 9' in order to hold together the diaper in the desired pant-like shape. The belt portions 9, 9' can be constituted for example of a laminate bonded in a suitable way of a carrier material 11 which on both sides is enclosed by receiving materials 12, 13, which can be nonwoven materials. These nonwoven materials can be identical or different. However, it is also conceivable with embodiments where the belt portions are constituted of a single material layer which both on the outside and the inside of the belt is able to serve as a receiving material for attachment means, for example in the form of hook material and/or adhesive tape. Thus, the attachment elements are partly the attachment material 10 on one of the belt portions 9 which is intended to be attached to the outside of the opposite belt portion 9', and partly the attachment elements 8, 8' on the front portion of the diaper, which are intended to be attached to the belt portions 9, 9' for holding together the diaper in the desired pant-shape. Thereby, the receiving area has to enable both release and reattachment of the attachment material both on the other belt portion 9 and on the attachment elements 8, 8'.

According to the invention, the attachment material 8a, 8b, 8'a, 8' is arranged on the attachment elements 8, 8' on both the first and the second main surface of at least one of the attachment elements when this is in an unfolded position, wherein the belt portion or the belt portions 9, 9' carries the receiving material 12, 13 across substantially the entire outside and inside. This provides an excellent adaptability to users with different body sizes and shapes, since preferably the entire outside and inside of the belt portions 9, 9' is able to serve as a receiving area for the attachment elements 8, 8' and attachment material 10 enabling release and reattachment of the attachment elements.

The attachment material 8a, 8b, 8'a, 8'b of the attachment elements 8, 8' is particularly advantageously constituted by a "hook material", but can also be constituted of adhesive tape or the like. As an attachment area for adhesive tape, usually a smooth or embossed plastic film is utilised, while nonwoven materials normally function well as (" loop material") an attachment area for the hook material. As has become evident in the foregoing, it also should be possible to release and reattach the attachment means. A nonwoven material as an attachment area for hook fasteners can advantageously consist of continuous filaments, such as a spunbond material or a meltblown material of, for example, polypropylene, polyethylene or bicomponent fibres.

Figure 2:
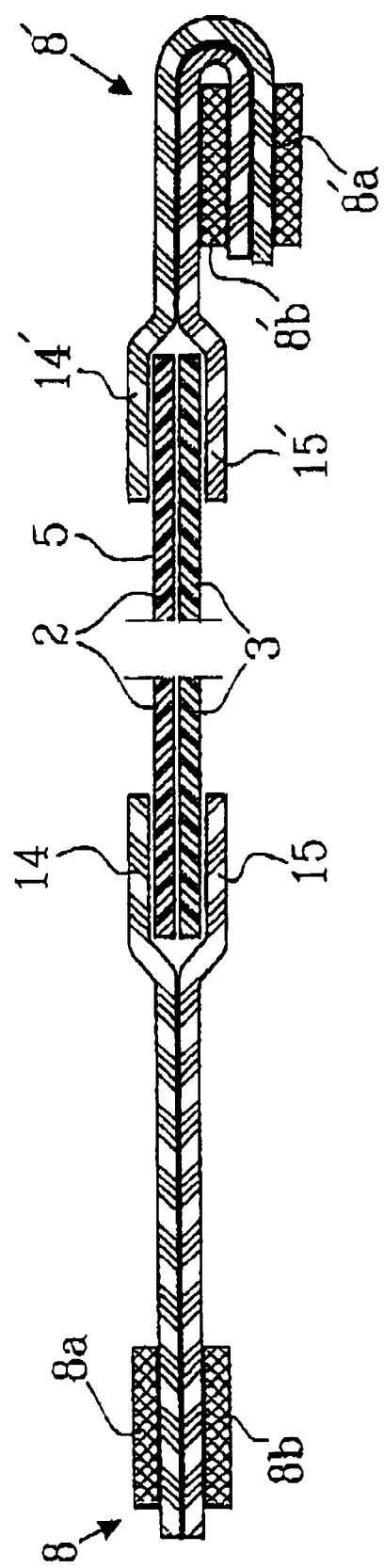

In a preferred embodiment of the absorbent article according to the invention, particularly illustrated in FIG. 2, one or several of the attachment elements 8, 9' comprise(s) additional receiving material 15, 15' which can serve as a receiving area for the attachment material 8b, 8'b on either the first or second main surface of the attachment elements 8, 8' when it is desired to bring the attachment means into a folded-in position. In the embodiment shown in FIG. 2, the material layers 14, 14' are a polyethylene film which, accordingly, advantageously can be replaced with an additional receiving material. Among other things, this embodiment provides the advantage that the attachment elements 8, 8' can be brought into a folded-in position during transport and storage in order to minimise the surfaces of attachment material which are exposed and accidentally may attach to the receiving material of the absorbent article. In FIG. 2, the risk of the attachment material 8'b accidentally being attached to a receiving material of the absorbent article has been eliminated by means of folding in the attachment element 8' against the additional receiving material 15', while the attachment material 8'a still is exposed. In order to eliminate exposed attachment material completely during transport and storage of the absorbent article, a removable, protecting tape or the like (not shown in FIG. 2) can be applied on those attachment surfaces which still are exposed when the attachment elements 8, 8' have been folded in.

It is also conceivable with embodiments (FIG. 1) where the outside and/or the inside of the belt portions 9, 9' serve(s) as a receiving area for different types of attachment elements 8, 8' and attachment material 10, for example in such a way that the attachment elements 8, 8' comprise hook material whereas the attachment material 10 is constituted of adhesive tape. At least the nonwoven material 13 which is to constitute the inside of the belt, i.e. be in direct contact with the skin of the user, should be soft and skin-friendly, for example a spun-bond material or a meltblown material of polypropylene or polyethylene, or a carded, thermobonded material. It is also conceivable with embodiments in which an elastic carrier material is included in the belt.

Figure 4:
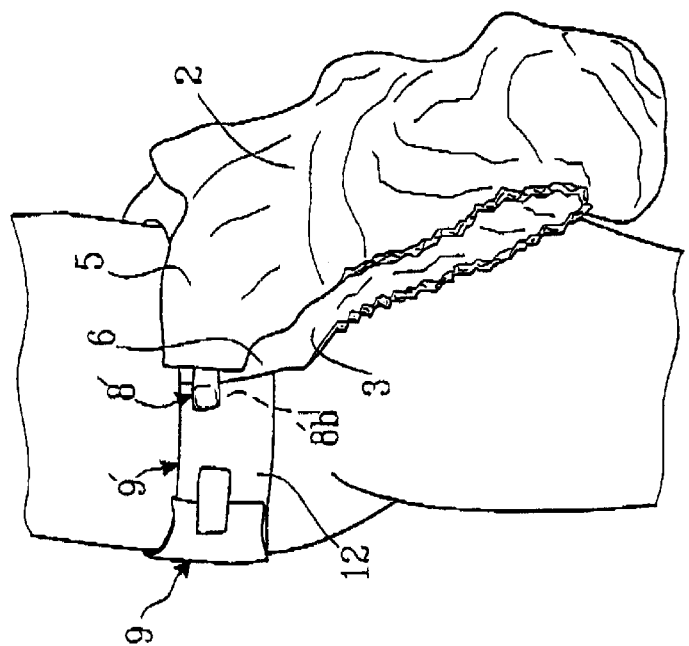
Figure 3:
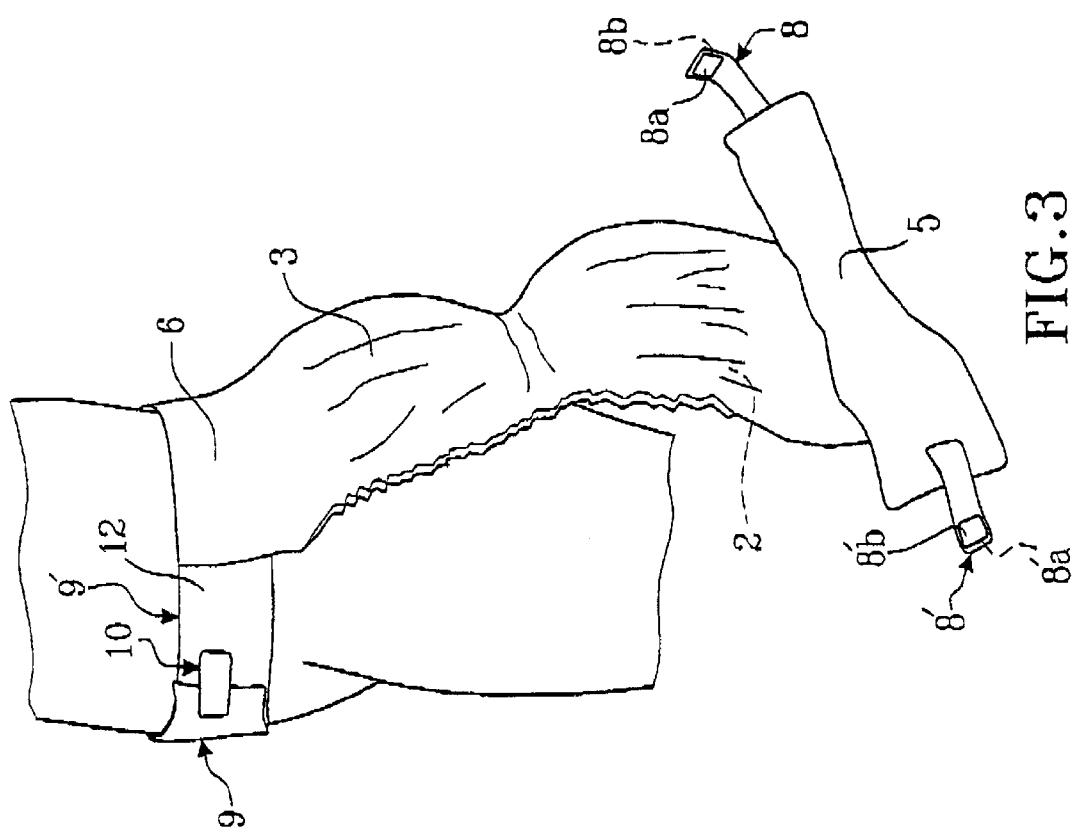

In a particularly preferred embodiment, illustrated in FIGS. 3 and 4, the attachment material on the second main surface 8'b is arranged so that, after the application of the belt portions 9, 9' on a user, the attachment material 8'b can be received by the receiving material 12 on the side which constitutes the outside of the belt portion 9 with the second main surface substantially in parallel to the plane of the receiving material 12 within the receiving area in order to suspend the front portion 5 of the article in the belt portion 9' with the front portion 5 on top of the rear portion 6 of the article. This embodiment provides the advantage that the attachment element 8' does not have to be turned around its axis or folded in order to be attached to the receiving material 12 of the belt in order to eliminate the problem with the article accidentally being dipped into a toilet bowl in connection with toilet training or a user's independent toilet visits.

In addition to making it easier for the user, in this embodiment a safer attachment of the attachment elements 8, 8' to the receiving material 12 is obtained than what has been possible previously.

Figure 6:
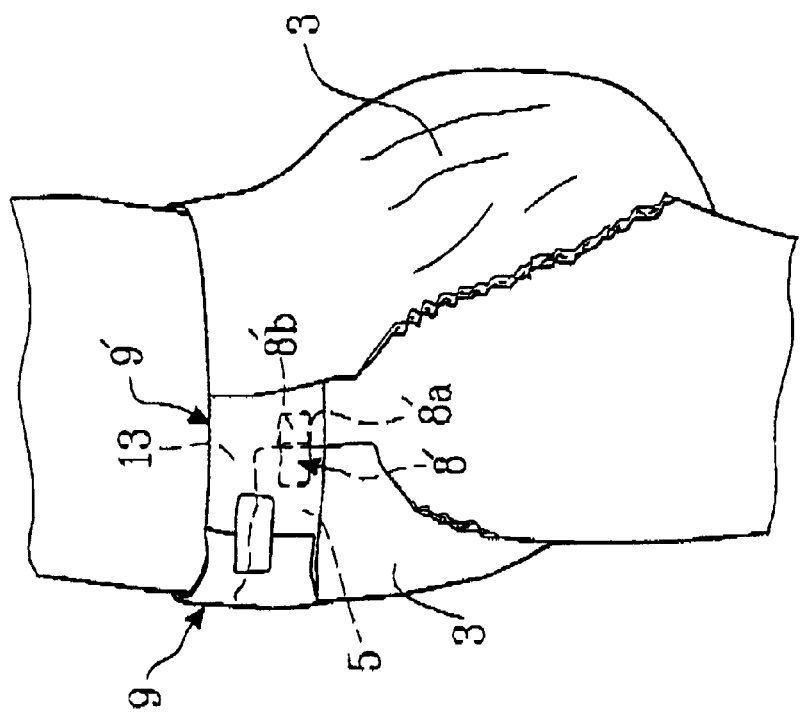
Figure 5:
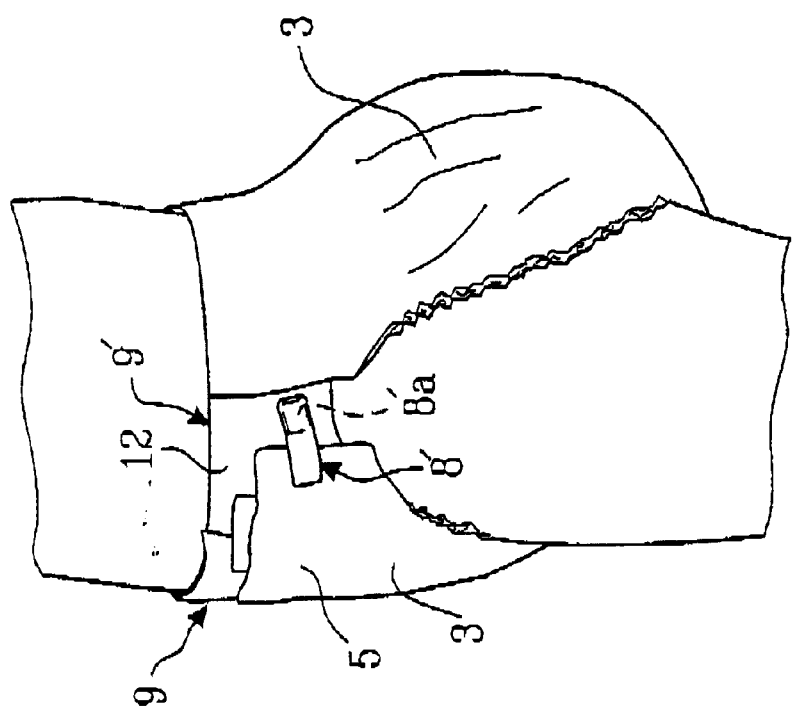

In another advantageous embodiment, particularly illustrated in FIG. 6, the attachment material on the second main surface 8b is arranged so that, when putting the article on a user as an all-in-one product, the attachment material 8'b can be received by the receiving material 13 on the side which is to constitute the inside of the belt portion 9' with the second main surface substantially parallel to the plane of the receiving material 13 within the receiving area. This embodiment advantageously can be utilised when a user or nursing staff for some reason prefer application as an 4-in-one product to application as a belt product.

In still another advantageous embodiment, not explicitly shown but still described with reference to FIG. 6, at least one of the attachment elements 8' is in the folded-in position with the attachment material on the second main surface 8'b received by the additional receiving material 15', wherein the attachment material on the first main surface 8'a is arranged so that, when putting the article on a user in a similar fashion as a pant diaper, the attachment material on the first main surface 8'a can be received by the receiving material 13 on the face which is to constitute the inside of the belt portion 9'. Since the attachment elements 8, 8', due to their being folded-in, get a reduced length and flexibility, this embodiment enables the front portion 5 of the absorbent article to be retained in a particularly stable way beneath the belt portions 9, 9' in those cases when the absorbent article already before being put on is to be attached in a pant diaper-like fashion.

The invention is of course not limited to the above-described embodiments, but can be modified within the scope of the claims.

What is claimed is:

1. An absorbent article, comprising a liquid-pervious topsheet, a liquid-impervious backsheet, and an absorbent body enclosed therebetween, the article includes a front portion, a rear portion and a crotch portion located therebetween, and further includes a belt attached to or intended to be attached to the rear portion and to the front portion of the article in such a way that the article assumes a pant shape where the belt constitutes a part of a waist portion of the pant, at least a first portion of the belt includes an outside face and an inside face and both the outside face and the inside face carry a receiving material which is adapted to serve as a receiving area and attach to an attachment material arranged on a second portion of the belt, the receiving material also is adapted to serve as a receiving area and attach to an attachment material arranged on at least one attachment element attached to the front portion of the article, the at least one attachment element has a first main surface and an opposite, second main surface on a reverse side thereof, and said receiving material also enables reattachment of said attachment material, wherein the attachment material on said at least one attachment element is arranged on both the first main surface and the second main surface of the at least one attachment element when the attachment element is in an unfolded position, and said first belt portion carries said receiving material across substantially its entire outside face and inside face.

2. The absorbent article according to claim 1, wherein said at least one attachment element comprises additional receiving material which is adapted to serve as a receiving area for said attachment material on the first or second main surface of the attachment element.

3. The absorbent article according to claim 1, wherein the attachment material on the second main surface is arranged so that, after applying the belt onto a user, said attachment material is adapted to be received by the receiving material on the outside face with said second main surface substantially parallel to a plane of said receiving material within said receiving area in order to suspend the front portion of the article from said belt with said front portion on top of the rear portion of said article.

4. The absorbent article according to claim 1, wherein the attachment material on the first main surface is arranged so that, when putting the article on a user, said attachment material can be received by the receiving material on the outside face with said first main surface substantially parallel to a plane of said receiving material within said receiving area.

5. The absorbent article according to claim 1, wherein the attachment material on the second main surface is arranged so that, when putting the article on a user as an all-in-one product, said attachment material is adapted to be received by the receiving material on the inside face with said second main surface substantially parallel to a plane of said receiving material within said receiving area.

6. The absorbent article according to claim 2, wherein the at least one attachment element is in a folded-in position with the attachment material on the second main surface received by the additional receiving material, wherein the attachment material on the first main surface is arranged so that, when putting the article on a user as a pant diaper, said attachment material on the mains surface can be received by the receiving material on the inside face.

7. The absorbent article according to claim 1, wherein the attachment material of said belt or of said attachment element is constituted of hook material or adhesive tape.

8. The absorbent article according to claim 1, wherein the receiving material of said belt or the additional receiving material of said attachment element is made of continuous filaments.

9. The absorbent article according to claim 8, wherein the continuous filaments are spunbond material.

10. The absorbent article according to claim 8, wherein the continuous filaments are meltblown material.

11. The absorbent article according to claim 1, wherein the article is a diaper.

12. The absorbent article according to claim 1, wherein the article is an incontinence guard.

* * * * *

UNITED STATES PATENT AND TRADEMARK OFFICE
CERTIFICATE OF CORRECTION

| | |
|---|---|
| PATENT NO. | : 6,669,678 B2 |
| APPLICATION NO. | : 09/814941 |
| DATED | : December 30, 2003 |
| INVENTOR(S) | : Kent Hermansson et al. |

It is certified that error appears in the above-identified patent and that said Letters Patent is hereby corrected as shown below:

Title Page add Foreign Application Priority Data as follows:

(30) Foreign Application Priority Data

March 31, 2000 - Sweden - 0001176-7

Signed and Sealed this

Twenty-third Day of October, 2007

JON W. DUDAS
*Director of the United States Patent and Trademark Office*